United States Patent [19]

Mishiro et al.

[11] Patent Number: 5,766,867
[45] Date of Patent: Jun. 16, 1998

[54] NON-A, NON-B HEPATITIS RELATED NUCLEIC ACIDS, PROTEINS, PEPTIDES, ANTIGENS, AND ANTIBODIES

[75] Inventors: Shunji Mishiro; Tetsuo Nakamura, both of Tokyo, Japan

[73] Assignee: Immuno Japan Inc., Tokyo, Japan

[21] Appl. No.: 394,326

[22] Filed: Feb. 23, 1995

Related U.S. Application Data

[63] Continuation-in-part of Ser. No. 653,090, Feb. 8, 1991, abandoned, Ser. No. 798,226, Nov. 27, 1991, abandoned, and Ser. No. 828,669, Feb. 7, 1992, abandoned.

[30] Foreign Application Priority Data

| Feb. 9, 1990 | [JP] | Japan | 2-028191 |
| Jun. 14, 1990 | [JP] | Japan | 2-153887 |
| Nov. 30, 1990 | [JP] | Japan | 2-335806 |
| Feb. 8, 1991 | [JP] | Japan | 3-104010 |

[51] Int. Cl.$^6$ .......................... G01N 33/53; G01N 33/576
[52] U.S. Cl. .................. 435/7.92; 435/5; 435/7.1; 435/7.9; 435/7.94; 435/7.95; 435/810; 530/388.1; 530/389.1; 530/387.1; 530/391.1; 436/547; 436/548; 424/130.1; 424/141.1
[58] Field of Search ........................ 435/7.92, 7.1, 435/5, 810, 7.9, 7.94, 7.95; 530/391.1, 388.1, 389.1, 387.1; 436/547, 548; 424/130.1, 141.1

*Primary Examiner*—Laurie Scheiner
*Attorney, Agent, or Firm*—Beveridge, DeGrandi, Weilacher & Young, L.L.P.

[57] ABSTRACT

Novel nucleic acids, proteins, peptides, antigens, and antibodies related to non-A, non-B hepatitis, and non-A, non-B hepatitis diagnostic reagents using those materials.

3 Claims, 10 Drawing Sheets

Fig. 1

λgt11 ............ ACTGATGGAA ACCAGCCATC GCCATCTACT GCACACGGAA GAAGAAGGCA

CATGGGCTGAA TATCGACGGT TTCCATATGG GGATTGGTGG CGACGACTCC TGGAGCCCGT

CAGTATCGGC GGAATTCC|CC TGTCCACCTC GCCGCAAGGC CAAAGAAACC GGAGCAGTCG
          EcoR I    └─ GOR47-1 Insert

ACGGCAGGAG AGGGCAAAAA GCCAAGAGTA ACCCCAACCG GCCACTCCCA GTCCCCCGGA

ATCCCTGCCG CGGACCCTCG GGCCTGTCCC CATCCCCTCTG CCCTTCCCCAG ACCTCTGTCC

TTCC|GGAATT CCAGCTGAGC GCCGGTCGCT ACCATTACCA GTTGGTCTGG TGTCAAAAAT
    EcoR I

AATAATAACC GGGCAGGCCA TGTCTGCCCG TATTTCGCGT AAGGAAATCC ............

Fig. 3

GOR47-1

```
          primer G1
CCTGTCCACC TCGCCGCAAG   GCCAAAGAAA CCGGAGCAGT   CGACGGCAAG AGAGGGCAAA
GGACAGGTGG AGCGGCGTTC   CGGTTTCTTT GGCCTCGTCA   GCTGCCGTTC TCTCCCGTTT AAGCCAAGAC TAAACCCCAAC  CGGCCACTCC CAGTCCCCCG   GAATCCCTGC CGCCGGACCCT
TTCGGTTCTC ATTGGGGTTG   GCCGGTGAGG GTCAGGGGGC   CTTAGGGACG GCGCCTGGGA CGGGCCTGTC CCCATCCCTC   TGCCCTTCCC AGACCCTCTGT  CCTTCC
GCCCGGACAG GGGTAGGGAG   ACGGGAAGGG TCTGGAGACA   GGAAGG
                                     primer G2
```

Fig. 9

```
λgt11 β-galactosidase ORF
............CTGATGGAAACCAGCCATGCGCCATCTACTGCACACGGAAGAAGAAGGCA
             L  M  E  T  S  H  R  H  L  L  H  T  E  E  E  G CATGGCTGAATATCGACGGTTTCCATATGGGGATTGGTGGGGACGACTCCTGGAGCCCGT
 H  G  F  H  M  G  I  G  G  D  D  S  W  S  P
  T  W  L  N  I  D  G  F  H  M  G  I  G  G  D  D  S  W  S  P
                           → GOR47-1 ORF
CAGTATCGGCGCGAATTCCCCTGTCCAAGGCCAAAAGAAACCGGAGCAGTCG
                    P  C  P  P  R  R  K  A  K  E  T  G  A  V
  S  V  S  A  E  F  P  C  P  P  R  R  K  A  K  E  T  G  A  V ACGGGCAGGAGAGGGCAAAAAGCCAAGAGTAACCCCAACCCGGCCCAGTCCCCCCGGA
 T  G  R  R  G  Q  K  A  K  S  N  P  N  R  P  L  P  V  P  R
  D  G  R  R  G  Q  K  A  K  S  N  P  N  R  P  L  P  V  P  R ATCCCCTGCCGCGGACCCTCGGGCCTATCCTCCCCATCCCCTATGCCCTTCCAGACCTCTGTCC
 I  P  C  R  G  P  S  G  L  S  P  S  L  C  P  S  Q  T  S  V
  N  P  C  R  G  P  S  G  L  S  P  S  L  C  P  S  Q  T  S  V TTCCGGAATTCCAGCTGAGCGCCGGTCGCCGGTACCATTACCAGTTGGTCTGTGTCAAAAA
 L  P  F  Q  L  S  A  G  R  Y  H  Y  Q  L  V  W  C  Q  K
  E  F  Q  L  S  A  G  R  Y  H  Y  Q  L  V  W  C  Q  K
↓
AATAA CCCGGGCCAGGCCCATGTCTCCCCGTATTTCGCCTAAGGAAATCC
stop codons
```

NON-A, NON-B HEPATITIS RELATED NUCLEIC ACIDS, PROTEINS, PEPTIDES, ANTIGENS, AND ANTIBODIES

REFERENCE TO RELATED APPLICATIONS

The present invention is a continuation-in-part of U.S. patent application Ser. No. 07/653,090, filed Feb. 8, 1991, now abandoned, U.S. patent application Ser. No. 07/798,226, filed on Nov. 27, 1991, now abandoned, and U.S. patent application Ser. No. 07/828,669, filed on Feb. 7, 1992, now abandoned. The above applicatons are relied on and incorporated by reference in their entirety.

INTRODUCTION TO THE INVENTION

The present invention relates to novel nucleic acids, proteins, peptides, antigens, and antibodies related to non-A, non-B hepatitis, and non-A, non-B hepatitis diagnostic reagents using those materials.

The causative agent of non-A, non-B hepatitis (hereinafter NANB hepatitis) afflicts human beings with such diseases as acute hepatitis, fulminant hepatitis, chronic hepatitis, liver cirrhosis and hepatocellular carcinoma. It presents itself as the major cause of post transfusion hepatitis in approximately 10% of the blood recipients in Japan. The causative viruses of hepatitis A and hepatitis B have been isolated and these diseases are under medical control. However, the causative agent of NANB hepatitis is a mystery although its presence was assumed over 10 years ago.

In 1988, a research group at Chiron Corporation in the United States announced that they had succeeded in cloning the gene of the causative agent of NANB hepatitis, and introduced an immunoassay kit for detection of antibody specific to NANB hepatitis. That diagnostic reagent is now being evaluated at various hospitals, research institutions and blood centers. According to Chiron's research group, the causative agent is a Flavivirus because of its genomic structure, and they have named it hepatitis C virus (HCV). The data reported to date have confirmed a good correlation between HCV antibody detected by their immunoassay kit and the course of the disease of NANB hepatitis. With respect to the HCV antibody, however, there are problems yet to be solved and elucidated: its insufficient specificity and sensitivity (revealed in several reports), cross reaction between HCV and a large part of auto-immune hepatitis and hepatitis B, and proof that what they call HCV is the real causative agent of NANB hepatitis.

Non-A, non-B hepatitis specific diagnostic assays based on detection systems using the present invention in this and preceding applications (Japanese Patent Application Nos. 028191/90 filed Feb. 9, 1990; 153887/90 filed Jun. 14, 1990; 335806/90 filed Nov. 30, 1990; and 104010/91 filed Feb. 8, 1991) are capable of detecting NANB patients not detected by the kit using Chiron's antigen (Ortho HCV Ab ELISA test: Ortho Diagnostic Systems, Tokyo, Japan).

SUMMARY OF THE INVENTION

An object of the present invention is to provide previously unidentified nucleic acids, proteins, peptides, antigens and antibodies required for detection and diagnosis of NANB hepatitis.

Nucleic acids and proteins disclosed in the present invention have usefulness in the diagnosis of NANB hepatitis and have been provided only by this invention as totally new materials. Nucleotide sequences and amino acid sequences of nucleic acids and proteins under this invention are in no way homologous to those of Chiron's HCV genome (European Patent Application No. 88310922.5).

The present invention discloses GOR gab DNA having the sequence as shown in sequence list 1 (SEQ ID NO:1); GOR gab protein having the sequence as shown in sequence list 2 (SEQ ID NO:2); GOR47-1 RNA having the sequence as shown in sequence list 3 (SEQ ID NO:3); GOR 47-1 RNAC having the sequence as shown in sequence list 4 (SEQ ID NO:4); GOR47-1 DNA having the sequence as shown in sequence list 5 (SEQ ID NO:5); GOR47-1 DNAC having the sequence as shown in sequence list 6 (SEQ ID NO:6); GOR47-1 Protein having the sequence as shown in sequence list 7 (SEQ ID NO:7); oligopeptide spGOR1 having the sequence as shown in sequence list 8 (SEQ ID NO:8); oligopeptide spGOR2 having the sequence as shown in sequence list 9 (SEQ ID NO:9); oligopeptide spGORa-epi having the sequence as shown in sequence list 10 (SEQ ID NO:10); oligopeptide spGORb-epi having the sequence as shown in sequence list 11 (SEQ ID NO:11); peptides containing 10 or more amino acids residues of GOR gab protein or GOR 47-1 protein (any peptide sequence containing 10 or more consecutive amino acids can be utilized so long as the sequences elicit antibodies recognizing NANB related antigens); monoclonal or polyclonal antibodies reactive against such proteins or peptides and methods of making such antibodies by immunization of animals with such proteins or peptides; methods of using such protein or peptides to prepare such antibodies; methods for detecting non-A, non-B hepatitis related nucleic acids in a sample; methods for detecting non-A, non-B hepatitis related antibodies in a sample; methods for detecting non-A, non-B hepatitis related antigens in a sample; non-A, non-B hepatitis diagnostic test kits for analyzing samples for the presence of antibodies directed against a non-A, non-B hepatitis related antigen; non-A, non-B hepatitis diagnostic test kits for analyzing samples for the presence of a non-A, non-B hepatitis related antigen.

BRIEF DESCRIPTION OF THE DRAWINGS

The present invention will be further understood with reference to the drawings, wherein:

FIG. 1 shows the base sequence of recombinant lambda-gt11 phage DNA to assemble GOR-47 DNA in EcoRI cleavage. Sequence within the frame is GOR47-1 DNA and those on the left and right sides of the frame are lambda-gt11 DNA.

FIG. 3 shows G1 and G2 used as primers for PCR.

FIG. 9 shows ORF and amino acid sequence of fusion protein produced by recombinant GOR47-1 lambda-gt11. Sequence within the frame is ORF and amino acid sequence of GOR47-1 PROTEIN.

DETAILED DESCRIPTION OF THE INVENTION

Figure 2:
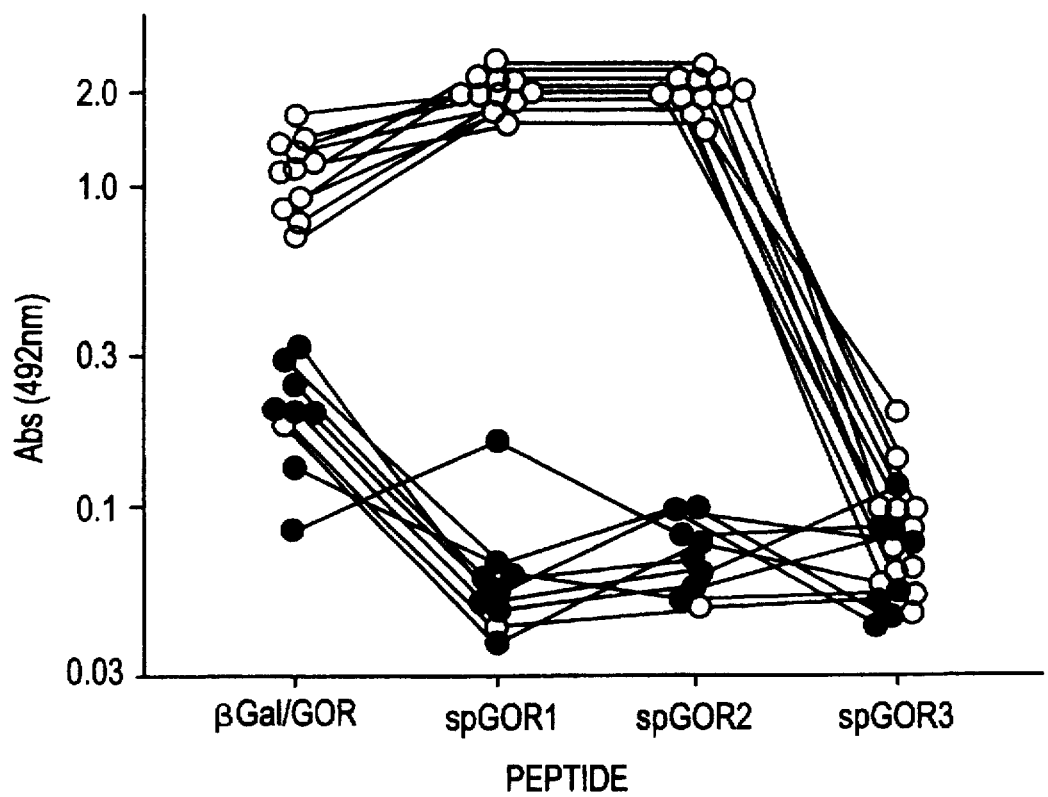
FIG. 2 shows reactivity the partial peptide on the ORF of GOR47-1 determined by EIA. Samples with ○ are NANB hepatitis and those with ● are hepatitis B derived; βGal/GOR is fusion protein of β-galactosidase and GOR47-1; spGOR3 is the peptide extended by 26 residues from the 15th residue of spGORa-epi toward C terminus and having the sequence (SEQ ID NO:12) LPVPRNPCRGPSGL-SPSLCPSQTSVL.
Figure 4A:
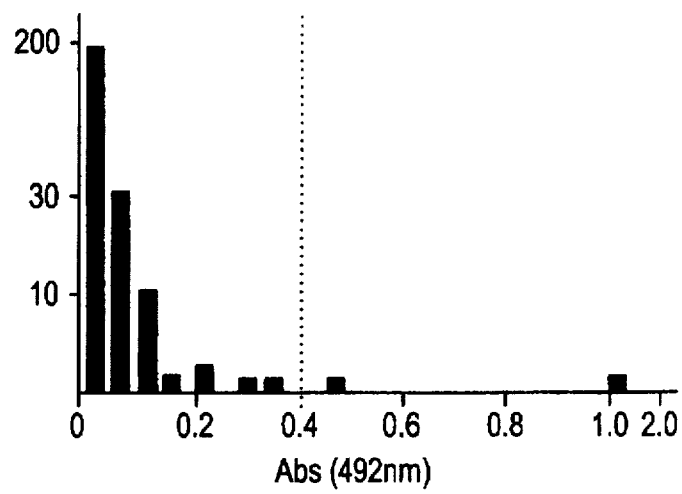
FIG. 4 is a histogram showing GORa antibody in samples from normal subjects and chronic hepatitis patients detected by EIA using spGOR2 as antigen. On the ordinate is samples from normal subjects and chronic hepatitis patients detected by EIA using spGOR2 as antigen. On the ordinate is shown frequency. Absorbance 0.4 at $OD_{492}$ is tentatively set as the cut-off value and shown by a dotted line. Positive rate for each group is as follows: (1) Normal subjects-1%; (2) NANB chronic hepatitis patients-76%; (3) Chronic hepatitis B patients-2%; (4) NANB liver cirrhosis-56%; (5) Hepatitis B liver cirrhosis-7%; (6) NANB hepatoma-56%; (7) Hepatitis B hepatoma-0%; (8) Lupoid hepatitis-0%; (9) Primary biliary cirrhosis-0%.
Figure 4B:
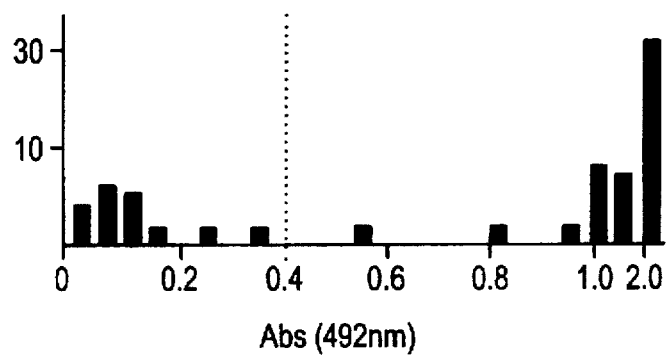
Figure 4C:
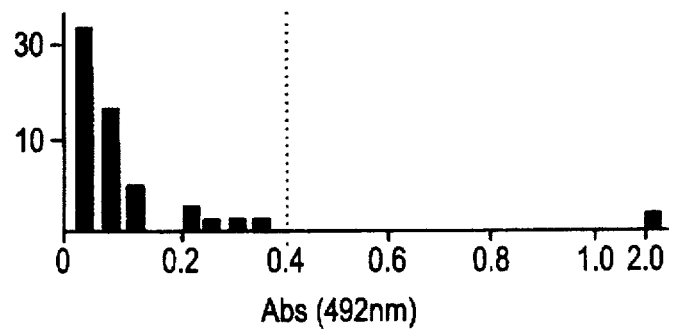
Figure 4D:
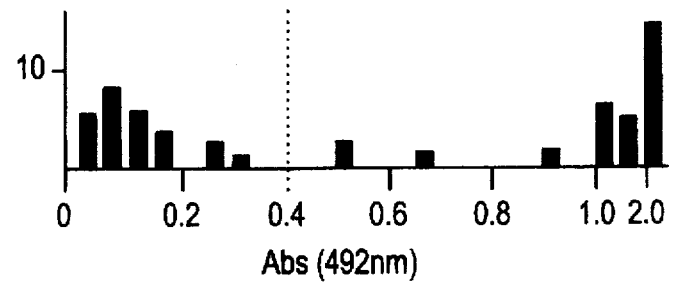
Figure 4E:
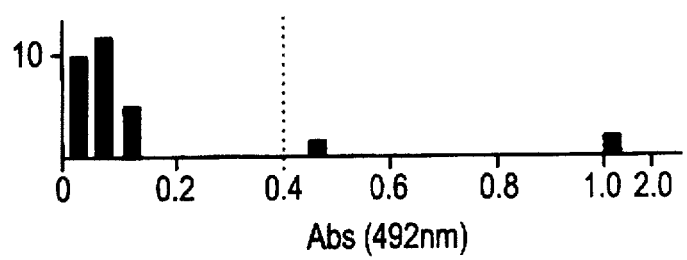
Figure 4F:
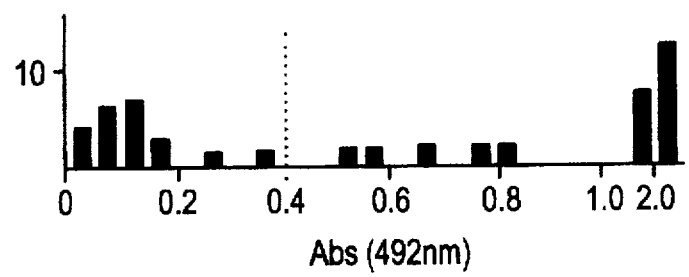
Figure 4G:
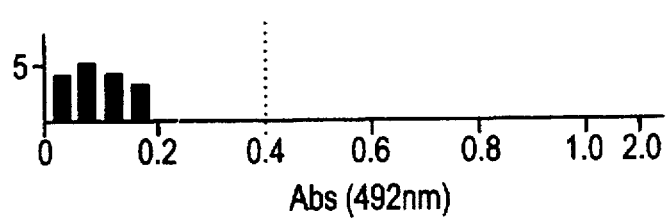
Figure 4H:
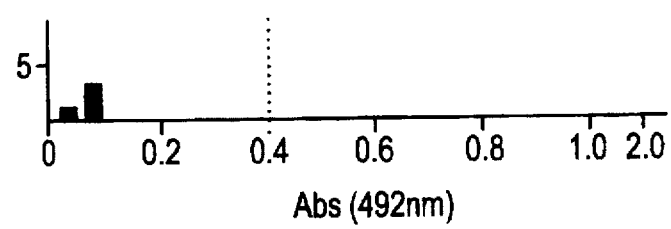
Figure 4I:
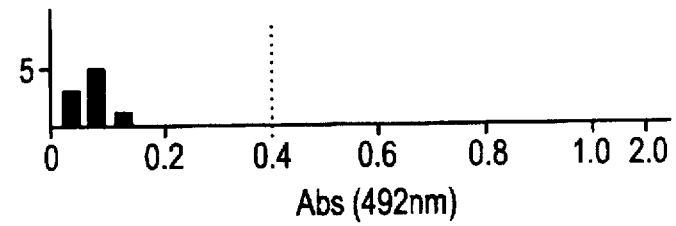

Features of the present invention reside in the following:

GOR gab DNA having the nucleotide sequence of SEQ ID:1.

GOR gab Protein having the amino acid sequence of SEQ ID NO:2.

Ribonucleic Acid GOR47-1 RNA having the nucleotide sequence of SEQ ID NO:3.

Ribonucleic Acid GOR47-1 RNAC having the nucleotide sequence SEQ ID NO:4.

GOR47-1 RNAC is the complementary strand of GOR47-1 RNA.

Deoxyribonucleic Acid GOR47-1 DNA having the nucleotide sequence of SEQ ID NO:5.

GOR47-1 DNA is a DNA counterpart of GOR47-1 RNA.

Deoxyribonucleic acid GOR47-1 DNAC having the nucleotide sequence of SEQ ID NO:6.

GOR47-1 DNAC is the complementary strand of GOR47-1 DNA.

Additional features include the following:

Protein GOR47-1 PROTEIN having the amino acid sequence of SEQ ID NO:7.

Oligopeptide spGOR1 having the amino acid sequence of SEQ ID NO:8.

Oligopeptide spGOR2 having the amino acid sequence of SEQ ID NO:9.

Oligopeptide spGORa-epi having the amino acid sequence of SEQ ID NO:10.

Oligopeptide spGORb-epi having the amino acid sequence of SEQ ID NO:11. The 18 amino acid residues correspond to amino acid numbers 346–363 of GOR gab protein, while C-terminal (Y) was added for peptide design. Generally (Y) is tyrosine for radiolabelling, though another amino acid(s) can be utilized (e.g., cysteine) for combining with such a protein as alkaline phosphatase.

A, G, C, and U stand for Adenine, Guanine, Cytosine and Uracil respectively in the ribonucleic acids of this invention.

A, G, C, and T stand for Adenine, Guanine, Cytosine and Thymine respectively in the deoxyribonucleic acids of this invention.

C, P, R, K, A, E, T, G, V, D, Q, S, N, L, stand for Cysteine, Proline, Arginine, Lysine, Alanine, Glutamic acid, Threonine, Glycine, Valine, Aspartic acid, Glutamine, Serine, Asparagine and Leucine respectively in the proteins of this invention.

The following procedures were utilized:

(1) Preparation of animal models for NANB hepatitis.

Research started with preparation of animal models for NANB hepatitis. Various animals were injected with sera from donors which were known to have caused post transfusional NANB hepatitis in humans. Among those animals, only chimpanzees responded and expressed symptoms similar to human NANB hepatitis. In case of the experimental NANB hepatitis in chimpanzees, some characteristic ultrastructural changes (e.g., convoluted curved membrane, tubular structure, sponge-like structure, and microtubular aggregates) tend to appear in the cytoplasm of liver cells before clinical symptoms, thus making these ultrastructural changes a reliable marker. Experimental passage of NANB causative agent was undertaken from a human being to a chimpanzee, then from that chimpanzee to other chimpanzees.

(2) Material for isolation of NANB hepatitis related gene.

Human serum (No. 30017) was injected into a chimpanzee (C37) and the serum from that chimpanzee (in acute phase hepatitis) was injected into 5 chimpanzees (C41, C43, C45, C46 and C47). Among those 5 chimpanzees, plasma were taken from those in the phase positive for the aforementioned ultrastructural changes and pooled for injection into other animals including the chimpanzee CH19. Plasma taken from chimpanzee CH19 (in acute phase of NANB hepatitis) was used as the material for isolation of NANB hepatitis related gene.

(3) Extraction of nucleic acids form chimpanzee plasma.

About six liters of plasma from chimpanzee CH19 (in acute phase of NANB hepatitis) was centrifuged on a J6 rotor (Beckman) at 3,000 rpm for 30 minutes, and the resulting supernatant was centrifuged on a Ti-15 rotor (Beckman) at 4° C. at 30,000 rpm for 5.3 hours. The resulting precipitate was suspended in 120 ml of 50 mM Tris-Cl (pH7.5)/5 mM EDTA to obtain virus-rich fraction concentrated by approximately 50 times. After addition to 6 ml of this fraction (equivalent to 300 ml of the original plasma) of 6 ml of SDS/Proteinase K cocktail (400 mM NaCl/20 mM EDTA/4% SDS/100 mM Tris-Cl buffer (pH 8.0)/Proteinase K 2 mg/ml) and overnight incubation at 37° C., nucleic acids were extracted with phenol and precipitated by ethanol.

(4) cDNA synthesis.

Using ¼ in volume (equivalent to 75 ml of the original plasma) of the nucleic acids obtained under (3) above, cDNA was synthesized. After incubation of the template RNA at 65° C. for three minutes, primary cDNA strand was synthesized in two tubes, one tube with oligo-$dT_{12}$ and the other tube with randam-hexanucleotide as primer. This series of cDNA synthesis, including synthesis of the secondary cDNA strand and blunting of double-stranded DNA termini, was conducted according to Gubler's method using a cDNA kit (Amersham, U.K.).

(5) Preparation of cDNA library.

After protecting possible EcoRI cleavage sites in the double-stranded cDNA prepared in (4) above by EcoRI methylase, providing both ends with EcoRI linker, it was integrated into lambda-gt11 DNA at the EcoRI site and assembled with phage protein to make recombinant phage. Series of this reaction was processed using the lambda-gt11 cloning kit (Amersham, U.K.). Library size of cDNA primed by oligo $dT_{12}$ and that of cDNA primed by randam-hexanucleotide were $1.0 \times 10^6$ PFU and $4.3 \times 10^6$ PFU respectively.

(6) Screening of cDNA library cDNA libraries prepared under (5) were searched for a NANB hepatitis related cDNA clone by immunoscreening using two antibodies. After infecting *E. coli* Y1090 with the above recombinant phage, and dispensing it on LB-Agar plates for incubation at 43° C. for three hours, a filter impregnated with IPTG was placed on it and incubated at 37° C. for three hours. The filter was then removed and washed with the buffer and primary antibody was added to it. A mixture of plasma of a chimpanzee infected with NANB hepatitis, a human plasma known to have caused NANB hepatitis by needle stick accident, and a plasma of chronic NANB hepatitis patient were used as the primary antibody, and incubated at 4° C. overnight. After washing with the buffer and addition of the secondary antibody (peroxidase labeled antihuman IgG), it was incubated at room temperature for 30 minutes. It was then washed with the buffer and added with the mixture of DAB (3,3-Diaminobenzidine tetrahydrochloride; Sigma, USA), Ni, Co, $H_2O_2$ for color development. If there were fractions of NANB related genes in the cDNA libraries, and if they fused with the open reading frame (ORF) of β-galactosidase of lambda-gt11 phage DNA in-frame, there should be fusion protein expressed by *E. coli* infected with the phage and, upon its recognition by NANB related antibody, it would bind to the antibody to give a positive signal. Inventors' experiment confirmed that point.

Among several clones giving positive signals in the screening test, there was a clone named GOR47-1 described hereafter.

(7) Determination of the nucleotide sequence of NANB hepatitis related cDNA clone (GOR47-1).

The nucleotide sequence of GOR47-1 obtained under (6) above was determined by Sanger's method by purifying it, cleaving its DNA by EcoRI to take out cDNA, and subcloning it to EcoRi site of Phagescript (trade name of Stratagene, USA). By means of primer derived from DNA phage, the nucleotide sequence at the insertion site of GOR47-1 was simultaneously determined in the same method. As a result, it was confirmed that GOR47-1 DNA was inserted into lambda-gt11 DNA by the sequence and direction shown in FIG. 1. FIG. 1 shows the nucleotide sequence of GOR47-1 with the junctional sequence of lambda-gt11 DNA. Sequence within the box is for GOR47-1 and those on the left and right sides of the box are for the lambda phage.

(8) Determination of the primary structure of the protein coded for by NANB hepatitis related cDNA clone (GOR47-1).

From the nucleotide sequence determined under (7) above, ORF of GOR47-1 linked with ORF of β-galactosidase of lambda-gt11 in frame was determined as per FIG. 9. Lambda-gt11 phage DNA used for preparation of cDNA libraries from which GOR47-1 was derived is a so called expression vector and expresses fusion protein of β-galactosidase and cDNA derived protein by assembling cDNA in operon of lacZ gene of lambda-gt11. Out of six possible reading frames, only one frame can fuse in frame with ORF of β-galactosidase of lambda-gt11 as shown in FIG. 9. There is no stop codon in this ORF encoding 55 amino acids. Under this invention, β-galactosidase can be replaced by expression proteins such as alkaline phosphatase and superoxide dismutase.

(9) Search for cDNA clone overlapping in sequence with NANB hepatitis related cDNA clone (GOR47-1).

From GOR47-1 phage, GOR47-1 DNA and GOR47-1 DNAC were cut out as insert DNA, and from recombinant phagescript obtained, GOR47-1 RNA and GOR47-1 RNAC were prepared by $T_3$ and $T_7$ promoters. They were all labeled with radioisotope. When they were used as probes to screen the cDNA libraries prepared under (5) above, cDNA clone (GOR gab DNA), while overlapping with GOR47-1, had a longer sequence. The base sequence of GOR gab DNA was determined in the same way as described above.

GOR gab DNA has the nucleotide sequence shown in SEQ ID NO:1. GOR 47-1 DNA corresponds to nucleic acid numbers 1703–1868 of GOR gab DNA.

(10) GOR gab protein encoded by NANB hepatitis related gene GOR gab DNA.

GOR gab protein which contains 661 amino acids was obtained by search for a sequence overlapping with GOR 47-1 ORF from six possible ORF which were coded in GOR gab DNA. SEQ ID NO:2 shows the amino acid sequence of GOR gab protein. The ORF coded by GOR 47-1 corresponds to amino acid numbers 569–623 in the sequence of GOR gab protein.

(11) Determination of NANB hepatitis related epitope (GORa) included in GOR aab Protein.

The following experiments were conducted using fusion proteins and synthetic peptides in order to determine NANB hepatitis related epitope.

(11-1) Purification of fusion protein made by NANB hepatitis related cDNA clone GOR47-1 and lambda-gt11 and β-galactosidase

*E. coli* Y1089 was lysogenically infected with the NANB hepatitis related gene (GOR47-1) obtained under (6) above to make lysogen. (Lysogen was prepared according to the method described in "Constructing and Screening cDNA Libraries in lambda-gt11", Thanh V. Huyuh et al., DNA Cloning, Vol. 1, a practical approach, ed. by D. M. Clover, pages 949–78, IRL Press, Oxford, 1985.) After culturing and inducing expression of protein by IPTG (isopropyl-β-D-thiogalactoside), and destruction of the lysogen by means of freezing-thawing and sonication, lysate was obtained and subjected to an affinity chromatography column (Sepharose 4B Immobilized IgG Fraction Rabbit anti-β-galactosidase; Cappel, USA) to obtain the fusion protein.

(11-2) Preparation of synthetic peptides originated in GOR47-1 ORF

The following three peptides were synthesized by Merrifield's solid phase method. Numbers indicate positions in the sequence of GOR gab protein.

spGOR1 (SEQ ID NO:8) Nos. 569–597 CPPRRKAKET GAVDGRRGQK AKSNPNRPL 29
spGOR2 (SEQ ID NO:9) Nos. 583–609 GRRGQKAKSN PNRPLPVPRN PCRGPSG 27
spGOR3 (SEQ ID NO:12) Nos.597–622 LPVPRNPCRG PSGLSPSLCP SQTSVL 26

(11-3) Epitope mapping by EIA (Enzyme Immuno Assay) and spGORa-epi

As described in the examples, antibody against fusion protein and synthetic peptides prepared in (11-1) and (11-2) above were detected by the EIA method. As FIG. 2 shows, fusion protein (β-Gal/GOR), spGOR1 and spGOR2 had identical antigenicity, but spGOR3 did not.

According to this result, epitope was identified as the following sequence of oligopeptide spGORa-epi (SEQ ID NO:10) shared with fusion protein and two synthetic peptides.

GRRGQKAKSNPNRPL Oligopeptide spGORa-epi was obtained by synthesis.

(12) Another epitope on GOR gab Protein, spGORb-epi.

The two most hydrophilic regions were found in GOR gab protein provided in (10) above. One of them was spGORa-epi of (11-3). Another region was revealed to have NANB hepatitis related epitope from the result of experiments concerning reactivity against antibody, when using synthetic peptide of the region, as shown in the examples.

The amino acid sequence of the synthetic oligopeptide, spGORb-epi, was as follows (SEQ ID NO:11):

VAKQHVRDGR KDSLDGFV(Y)

The 18 amino acid residues correspond to numbers 346–363 of GOR gab protein, while C-terminal (Y) was added for peptide design. Generally (Y) is tyrosine for radiolabelling, though another amino acid(s) can be utilized (e.g., cysteine) for combining with such a protein as alkaline phosphatase.

(13) Preparation of antibody specific to NANB hepatitis related antigen.

Monoclonal and polyclonal antibodies were obtained by immunizing, for example, mice, guinea pigs, goats, horses, or other animals with fusion proteins and synthetic peptides, GOR gab Protein, GOR 47-1 Protein, spGOR1, spGOR2, spGORa-epi and spGORb-epi bearing the NANB hepatitis related epitope which were determined under (11) and (12) above.

(14) Preparation of antigen assay by specific antibody to the NANB hepatitis related antigen.

Antibodies prepared under (13) above were labeled with FITC (fluorescein isothiocyanate) to make a probe for staining sample sections, such as liver tissue of patients infected with NANB hepatitis, to locate or examine locality of antigen specific to NANB hepatitis in tissue. An assay system was also developed by labelling specific antibodies with peroxidase or biotin to detect NANB hepatitis related antigen in patient's sera or plasma. This assay employs the "sandwich method" in which microplates or beads are coated with specific antibodies, and samples (e.g., human tissue or sera or plasma) and labeled antibodies are applied in sequence for reaction.

(15) Detection of NANB hepatitis related gene by Polymerase Chain Reaction (PCR).

According to the method described under (3) above, viral fractions were obtained by centrifugation of sample sera or plasma and subjected to PCR after treatment with SDS/Proteinase K cocktail and extraction of nucleic acid with phenol. Primer used for PCR was oligonucleotides G1 and G2, each consisting of 20 nucleotides as shown in FIG. 3 and located at both ends of NANB hepatitis related cDNA GOR47-1. G1 (SEQ ID NO:13) corresponds to 20 bases of 5' terminus of GOR47-1 DNA and is closest to 5' side of the sense strand, while G2 (SEQ ID NO:14) corresponds to 20 bases of 5' terminus of GOR47-1 DNAC and is closest to 5' side of anti-sense strand. As a result, the presence of PCR product of expected length (same 166 bases as GOR 47-1) was confirmed in both chimpanzee and human plasma which was suspected to be NANB hepatitis.

The nucleotide sequence of GOR gab DNA and GOR47-1 DNA and the deduced amino acid sequences bears no resemblance to the reported sequences of HCV. The GOR47-1 sequence was identified in a single copy gene of the host, as indicated by Southern blot and PCR (see Mishiro, S., et al., The Lancet (Dec. 8, 1990), volume 336, pages 1400–1403). Without being bound by theory, anti-GOR antibody is believed to be an auto-antibody since the autoimmune protein to which anti-GOR might be directed is a nuclear antigen.

EXAMPLES (1) GOR gab DNA.

The nucleotide sequence of NANB hepatitis related cDNA (GOR47-1) was determined in the following way:

GOR47-1 phage obtained in the above-mentioned (6) was purified, its DNA cleaved by EcoRI to obtain cDNA, that cDNA subcloned to EcoRI site of Phagescript (Stratagene, USA) and its nucleotide sequence determined by Sanger's method. Nucleotide sequence of the linking part of the insert arm of GOR47-1 phage DNA was similarly determined by the primer derived from the phage DNA. Those sequences revealed that GOR47-1 DNA was inserted in the lambda-gt11 DNA with the nucleotide sequence and direction shown in FIG. 1, and insert DNA, that is GOR47-1 DNA, was cut out from DNA47-1 phage DNA. FIG. 1 shows the nucleotide sequence of GOR47-1 together with its linking part with lambda-gt11 DNA. The sequence within the box is that of GOR47-1 and sequences on the right and left side of the box are those of lambda-gt11 DNA.

GOR47-1 DNA has the nucleotide sequence shown in SEQ ID NO:5.

In the similar way, GOR47-1 DNAC (having DNA complementary to strain GOR47-1 DNA) was cut out from GOR47-1 phage DNA. GOR47-1 DNAC has the nucleotide sequence shown in SEQ ID NO:6.

In the next step, GOR47-1 RNA and GOR47-1 RNAC (which have the nucleotide sequences shown in SEQ ID NO:3 and SEQ ID NO:4 respectively) were prepared from recombinant phage script of GOR47-1 DNAC using $T_3$ and $T_7$ promoters, they were labeled with radioisotope and used as probe to search the cDNA libraries prepared in (5) above, and GOR gab DNA, clone of cDNA, overlapping with but having longer sequence than GOR47-1, was obtained. The nucleotide sequence of GOR gab DNA (SEQ ID NO:1) was determined in the same way as above.

It is well known in the art that one or more nucleotides in a DNA sequence can be replaced by other nucleotides in order to produce the same protein. The present invention also concerns such nucleotide substitutions which yield a DNA sequence which codes for GOR gab Protein (the amino acid sequence of which is described above).

(2) GOR gab Protein.

From GOR gab DNA, GOR gab Protein coded by it was obtained. Lambda-gt11 phage DNA used for preparation of cDNA libraries from which GOR gab DNA was derived is a so called "expression" vector and expresses fusion protein of β-galactosidase and cDNA derived protein by assembling cDNA in operon of lacZ gene of lambda-gt11. Among possible reading frames of GOR gab DNA, only one reading frame fuses in frame with open reading frame (ORF) of β-galactosidase of lambda-gt11.

Amino acid sequence of GOR gab Protein is shown in SEQ ID NO:2. It is well known in the art that one or more amino acids in an amino acid sequence can be replaced by equivalent other amino acids, as demonstrated by U.S. Pat. No. 4,737,487 which is incorporated by reference in its entirety, in order to produce an analog of the amino acid sequence. Any analogs of GOR gab Protein of the present invention involving amino acid deletions, amino acid replacements, such as replacements by other amino acids, or by isosteres (modified amino acids that bear close structural and spatial similarity to protein amino acids), amino acid additions, or isosteres additions can be utilized, so long as the sequences elicit antibodies recognizing NANB antigens.

In this invention, β-galactosidase can be substituted by such expression proteins as alkaline phosphatase and superoxide dismutase.

(3) NANB hepatitis antigen related epitope by synthetic peptide based on the amino acid sequence coded for by GOR gab DNA.

Synthetic peptides of various lengths and for various regions based on the ORF of GOR gab DNA were prepared and examined for reactivity with NANB hepatitis related antibody to determined the location of NANB hepatitis epitope. Polystyrene microplates coated with synthetic peptide prepared by Merrifield's solid phase method as solid phase, sample sera as primary antibody, and peroxidase labeled anti-human IgG or IgM antibodies as secondary antibody for color reaction were used.

As a result, spGORa-epi and spGORb-epi were determined as NANB hepatitis related epitopes. SpGORa-epi has the amino acid sequence shown in SEQ ID NO:10 and spGORb-epi shown in SEQ ID NO:11. Furthermore,it has been found that peptides containing 10 or more amino acids residues have the antigen epitope; any peptide sequence containing 10 or more consecutive amino acids can be utilized so long as the sequences elicit antibodies recognizing NANB related antigens.

(4) NANB hepatitis related antibody detection system using proteins and peptides described above as antigen.

An example of experiments of NANB hepatitis related antibody detection system (Enzyme Immuno Assay) using GOR gab protein and peptides is shown below.

50 μl each of GOR gab Protein or peptides having 10 or more amino acids residues dissolved in Tris-HCl buffer (10 mM, pH 7.5) and adjusted to 5 μg/ml concentration was dispensed in each well on Costar vinyl plates (Toyobo, Japan) and incubated overnight at room temperature (coating of peptide). After washing the wells (0.1% Tween 20, 150 mM NaCl; all washing procedures hereafter in this experiment, unless otherwise stated, were with this solution), 100 μl each of the blocking solution (0.1% Tween 20, 150 mM NaCl, 30% fetal calf serum) was dispensed in the wells for overnight incubation at 4° C. on a vibration free. After washing the wells, 50 μl each of sample plasma, or serum preliminary diluted 30 times with the above-mentioned blocking solution, was dispensed in the wells for incubation at room temperature for 30 minutes on a vibrator. After washing the wells, 50 μl each of peroxidase labeled anti-human IgG or IgM mouse monoclonal antibody solution was dispensed in the wells for incubation at room temperature for 30 minutes on a vibrator, then peroxidase substrate solution was added for color development and absorbance measurement at wavelength 492 nm on a spectrophotometer.

(1) When samples from 100 chronic liver disease patients (mixture of hepatitis B and NANB hepatitis) were assayed by the EIA method, frequency by the assay using the protein or peptides under this invention turned out to be high for NANB chronic hepatitis, liver cirrhosis and hepatocellular carcinoma, while low for chronic liver disease, liver cirrhosis and hepatocellular carcinoma caused by hepatitis B virus, lupoid hepatitis of which autoimmune disorder was suspected, and primary biliary cirrhosis. The assay also showed low frequency for samples from normal subjects, thus proving the efficiency of the protein and peptides under the present invention for use in detection system of NANB hepatitis related antibody.

(2) As FIG. 4 shows, GORa antibody frequency detected by EIA using spGOR2 was as high as 76%, 56% and 56% for NANB related chronic hepatitis, liver cirrhosis and hepatoma respectively, while it was as low as 2%, 7% and 0% for hepatitis B related chronic hepatitis, liver cirrhosis and hepatoma respectively. It was 0% and 0% for lupoid hepatitis and primary biliary cirrhosis which were supposed to be closely associated with autoimmune mechanism, or was only 2 (1%) out of 200 for normal subjects. This proved a close relation of GORa antibody with NANB hepatitis.

Figure 5:
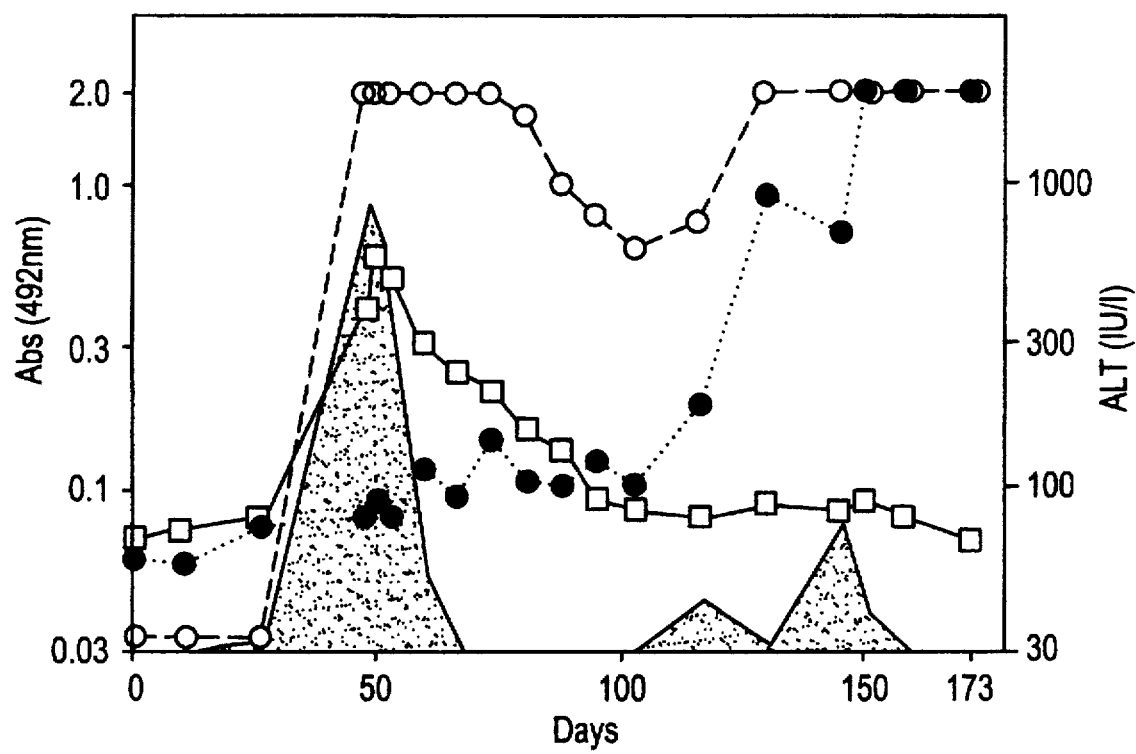
FIG. 5 shows change with time of GORa antibody in acute NANB hepatitis patients determined by EIA using spGOR2. ○: IgG class GORa antibody; ☐: IgM class GORa antibody; ●: HCV by Ortho HCV ELISA Ab test kit; black area: Serum ALT (alanine aminotransferase) value.

(3) Change of GORa antibody in an acute NANB hepatitis patient. GORa antibody positive frequency turned out very high for chronic hepatitis, liver cirrhosis and hepatoma as shown above, and the antibody appeared in very early period for acute hepatitis. A typical example of an outbreak of acute hepatitis is shown in FIG. 5 (needle stick accident in which a nurse stuck herself with an injection needle while drawing blood from a patient with NANB chronic hepatitis).

In this case, both IgM and IgG classes of GORa antibodies were detected on the 49th day after the needle stick accident while HCV antibody was detected (Ortho HCV Ab ELISA test; Ortho Diagnostic Systems, Japan) as late as on the 131st day after the accident. This has proven that GORa antibody is effective in early detection of infection.

GORa antibody could be derived from GOR 47-1 protein, spGOR1, spGOR2, and spGORa-epi.

(5) Detection of NANB hepatitis related antibody by the fusion protein containing NANB epitope spGORa-epi as antigen.

While the fusion protein of GOR 47-1 and lambda-gt11 - Ã-galactosidase was used, Ã-galactosidase can be substituted by expression proteins such as alkaline phosphatase and superoxide dismutase.

The fusion protein obtained above (11) was electrophoresed by SDS-PAGE and its pattern was transferred onto nitrocellulose membrane by the Western blotting technique. Sample plasma was applied onto this membrane and after incubation anti-human immunoglobulin labeled with peroxidase was added for detection of the antibody through color reaction.

The Western blotting method was used for detection system as follows: The nitrocellulose membrane with the electrophoresed pattern transferred onto it was rinsed for ten minutes, dried naturally, shredded into strips 3.5 mm wide, and those strips were immersed in TBS (50 mM Tris-Cl buffer, pH 7.4, 150 mM NaCl) containing 2% skim milk at room temperature for one hour or at 4½C overnight (blocking), then washed with TBST (TBS containing 0.05% Tween 20). After immersion at room temperature for one hour or at 4½C overnight in the primary antibody diluted 30 times with 3% BSA (primary antigen-antibody reaction), those strips were washed with TBST, immersed at room temperature for 30 minutes in biotinylated anti-human IgG or anti-human IgM (Vectastain ABC kit; Vector Laboratories Inc., USA) diluted with TBS (secondary antigen-antibody reaction), washed with TBST, then immersed in peroxidase labeled mixture of biotin and avidin (Vectastain ABC kit; Vector Laboratories Inc., USA) at room temperature for 30 minutes (biotin-avidin reaction), then washed with TBST followed finally by addition of coloring reagent to examine the presence of reactive substances. The coloring reagent was prepared by adding 25 mg of DAB (3,3'-Diaminobenzidine tetrahydrochloride; Sigma, USA) to 50 ml of 50 μM NaPO$_4$ pH7.4 and, after dissolution of DAB, 1 ml of 5% CoCl$_3$-6H$_2$O, 5% (NH$_4$)$_2$Ni(SO$_4$)$_2$6H$_2$O, then, 50 μl of 30% H$_2$O$_2$. When antibody was positive, a band of about 120K Dalton was stained dark blue.

Figure 6:
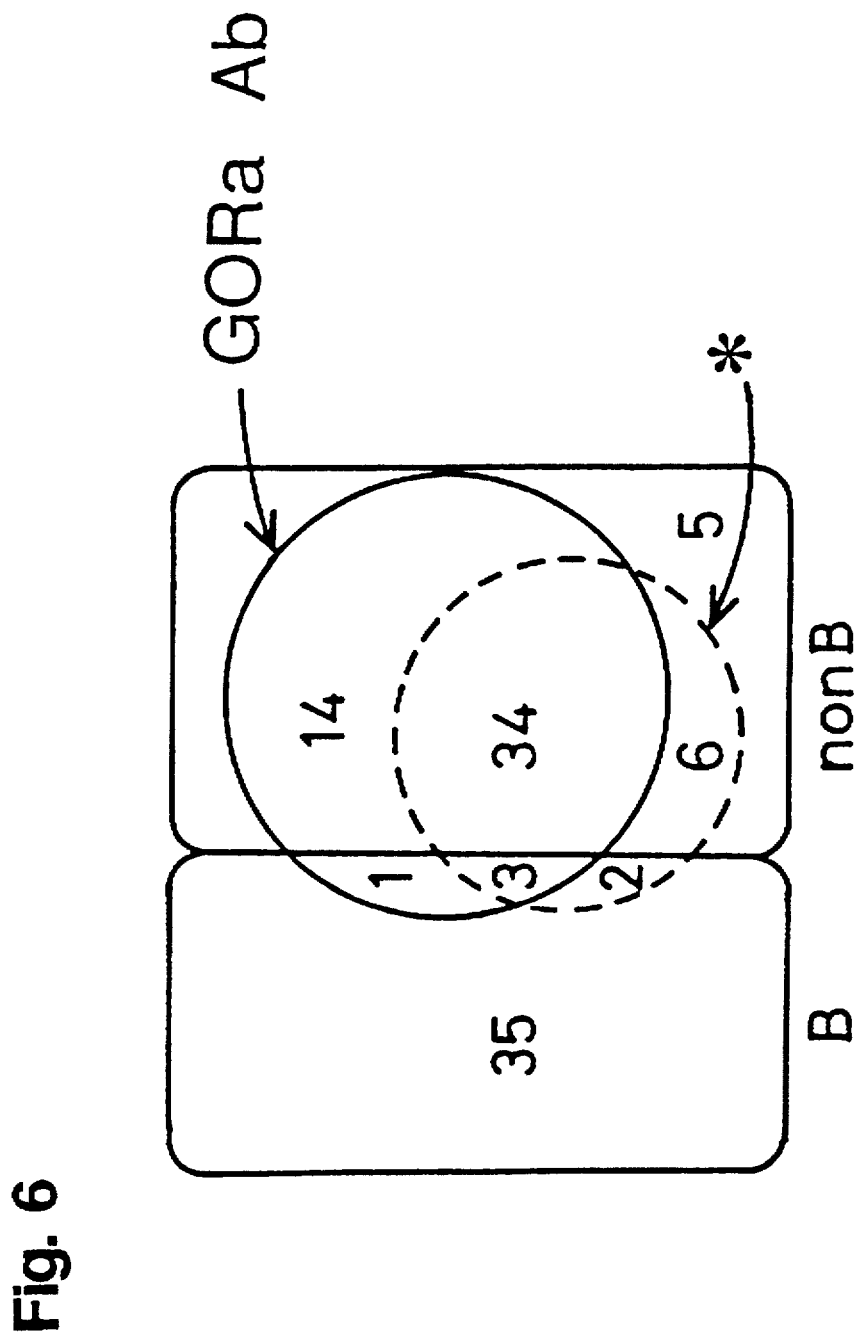
FIG. 6 is distribution pattern of chronic NANB hepatitis patient sera showing positive for GORa antibody. Sera positive for Chiron's HCV antibody are shown by * mark.

(1) Detectability of NANB Hepatitis Related Antibody (GORa Antibody) in Patients with Chronic Liver Diseases Sera of 100 patients with chronic liver diseases (40 cases of hepatitis B and 60 cases of non-B hepatitis) were assayed by the Western blot analysis. Results are shown in Tables 1 and 2, and FIG. 6. As shown in Tables 1 and 2, among 100 cases, GORa antibody was positive for 52 cases in total and its rate was much higher for the sera of non-B hepatitis cases (80%) than for the sera of hepatitis B cases (10%). Especially in chronic non-B hepatitis cases, GORa antibody was positive for 27 cases out of 30 cases (90%). When GORa antibody was compared with Chiron's HCV antibody (Ortho HCV Ab ELISA test; Ortho Diagnostic Systems, Tokyo, Japan), the former showed lower positive rate for the sera of hepatitis B cases (10%, 13%) and conversely higher positive rate for sera of NANB hepatitis cases (80%, 68%) than the latter. Furthermore, as shown in FIG. 6, there were 14 NANB hepatitis cases which GORa antibody detected but HCV antibody failed to detect, while there were only six converse cases.

(2) GORa Antibody in Sera From Donors Having Abnormal Liver Function

Frequency of GORa antibody and HCV antibody for sera of randomly selected 42 donors (ALT over 80, hepatitis B negative) were, as shown in Table 3, 20% and 17% respectively. Sera were tested in the method described in (1) immediately above. In five cases, both GORa antibody and HCV antibody were positive. ALT (alanine aminotransferase) level in serum is one of the markers which indicate liver function and is high (abnormal) when the host is infected with viral hepatitis, but it is also high when liver is malfunctioning due to some other causes such as alcohol, drugs, obesity, etc. The group consisting of 42 donors was consciously healthy but was unconsciously high in ALT level and differed from the groups in (1) above in that the cause of the high ALT level was not checked in this group while that of the groups in (1) was checked (chronic hepatitis, liver cirrhosis, or hepatoma). The difference in frequency of GORa antibody between this group and those in (1) may be attributed to this fact.

(3) Comparison of EIA for the Detection of GORa Antibody Using Synthetic Peptide and Western Blot Analysis Using Protein Fused with β-galactosidase 100 sera from patients with chronic type-B or type-NANB liver diseases were tested by EIA for GORa antibody and most of them turned out to be positive by both EIA and Western blot analysis, but 11 samples were positive by EIA but negative or weakly positive by Western blot analysis, suggesting that the former detects GORa antibody at higher sensitivity than the latter (Table 5).

(6) The Antibody Detection System Using spGORb-epi Which Contains NANB Hepatitis Related Epitope of the Invention, GORb, as Antigen was Prepared in the Same Method as in Example 1.

Figure 7A:
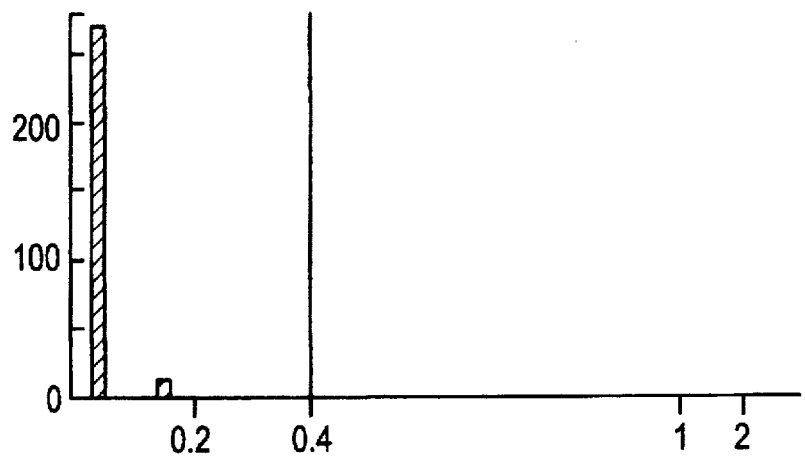
FIG. 7, a histogram, shows comparison of antibody to GORb epitope detection frequency using spGORb-epi in three groups: 1) normal subjects, 2) type-B liver diseases and 3) NANB hepatitis. On the ordinate is samples from normal subjects and chronic hepatitis patients detected by EIA using spGORb-epi as antigen. On the ordinate is shown frequency. Absorbance 0.4 at $OD_{492}$ is tentatively set as the cut-off value and shown by a dotted line.
Figure 7B:
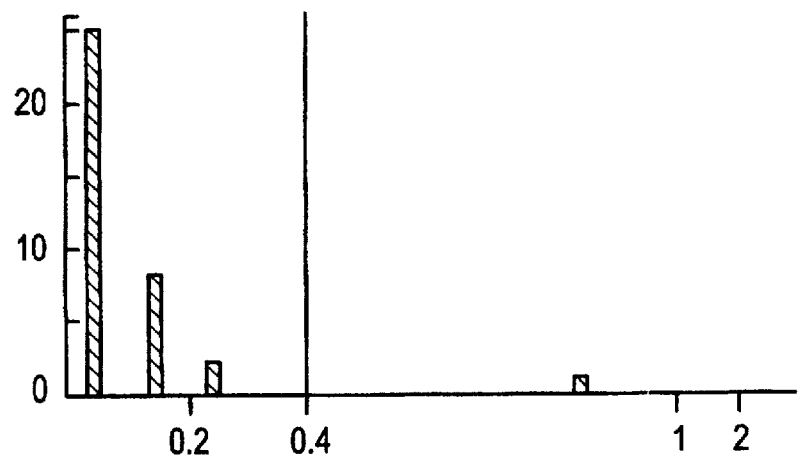
Figure 7C:
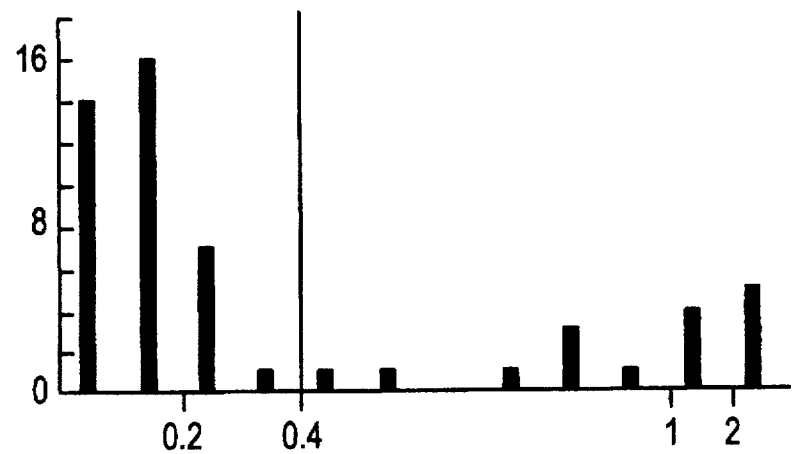

The results shows the efficiency of spGORb-epi for detection of NANB hepatitis as follows: GORb antibody was detected in 8 out of 290 cases (3%) in normal subjects, 1 out of 36 cases (3%) in type-B liver disease, and 17 out of 54 cases (31%) in NANB hepatitis as shown in FIG. 7 (cutoff value was $OD_{492}=0.4$.

(7) Preparation of Monoclonal and Polyclonal Antibodies

Specific monoclonal and polyclonal antibodies were obtained by immunizing, for example, such animals as mice, guinea pigs, rabbits, goats and horses with GOR gab Protein and the synthetic peptides bearing NANB hepatitis antigenic epitope described in the above example.

(8) Antigen Detection Assay Using Antibody Specific to NANB Hepatitis Related Antigen By staining tissue sections of liver, etc. from NANB hepatitis patients with the aforementioned specific antibody labeled with FITC as probe, the presence and locality of NANB hepatitis related specific antigen in tissue was examined. By labeling the specific antibody with peroxidase or biotin, assay system for detection of NANB related antigen in patient serum or plasma was developed. The system was the sandwich method in which polystyrene microplates or beads coated with NANB hepatitis related specific antibody were used as solid phase and after addition of samples (e.g., human tissue or plasma or sera) for reaction with the solid phase, labeled specific antibody was added for the second reaction.

Experiments of those assays confirmed the effectiveness of monoclonal and polyclonal antibodies under the present invention for detection of NANB hepatitis related antigen.

(9) Detection of NANB Hepatitis Related Gene by Polymerase Chain Reaction (PCR)

Figure 8:
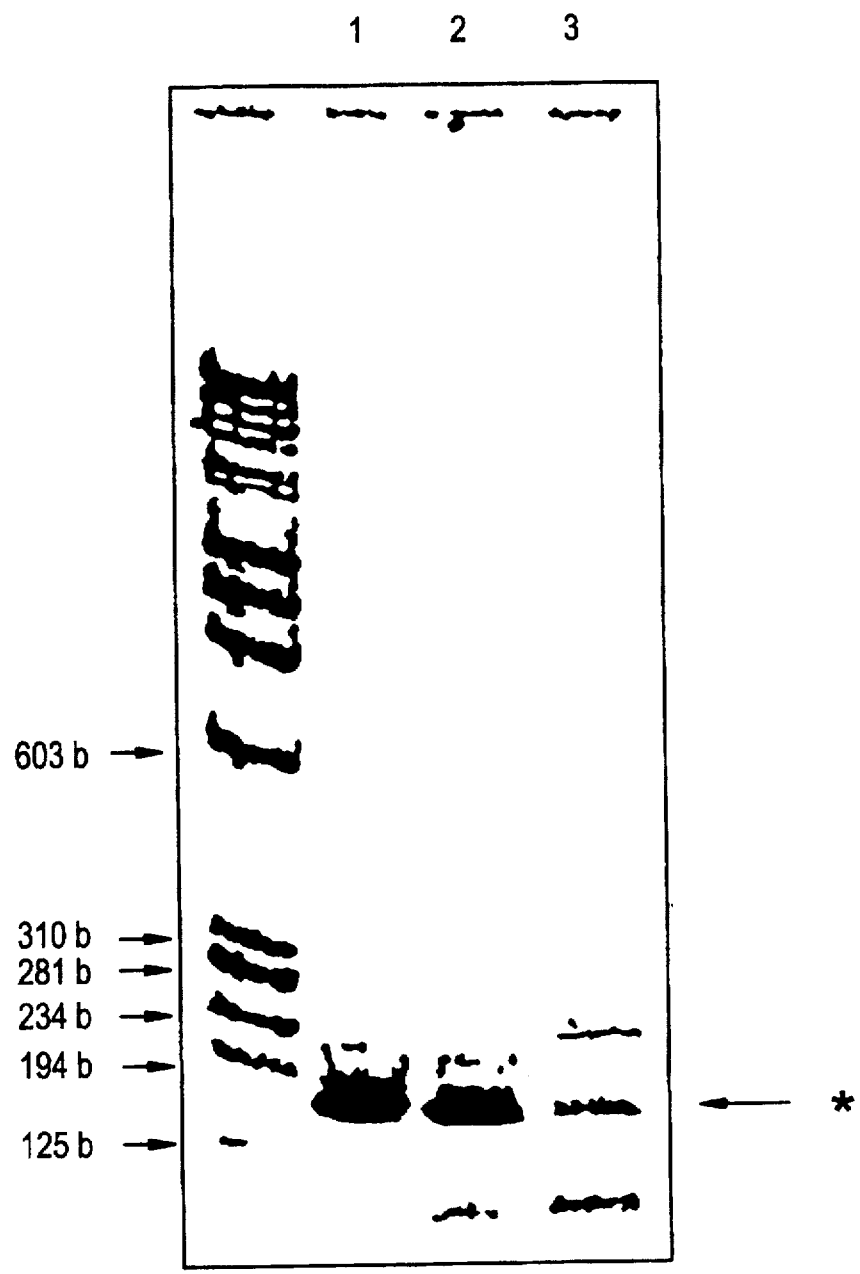
FIG. 8 shows agarose gel electrophoresis patterns of the material produced by PCR.

According to the method described under (3) above, viral fractions were obtained by centrifugation of sample sera or plasma and subjected to PCR after treatment with SDS/Proteinase K cocktail and extraction of nucleic acid with phenol. Primer used for PCR was oligonucleotide G1 and G2, each consisting of 20 nucleotides as shown in FIG. 3 and located at both ends of NANB hepatitis related cDNA GOR47-1. G1 corresponds to 20 bases of 5' terminus of GOR47-1 DNA and is closest to 5' side of the sense strand, while G2 corresponds to 20 bases of 5' terminus of GOR47-1 DNAC and is closest to 5' side of anti-sense strand. After addition of primer G2 (antisense) to the above mentioned nucleic acid fractions as the primary reaction in PCR, four nucleotides and transcriptase were added for reaction and synthesis of primary cDNA. Primer G1 was then added and the standard PCR reaction was followed for 36 cycles using Taq polymerase and the automatic temperature control unit (Cetus Corp., U.S.). The product (DNA) thus produced was separated by agarose gel electrophoresis and the presence of an expected length (same 166 bases as GOR47-1) of DNA fragment (identified by * in FIG. 8) was confirmed. Chimpanzee (CH19) plasma from which NANB hepatitis related cDNA clone GOR47-1 was derived contained PCR product of 166 bases (FIG. 8, Lane 1). A similar band was separated from the plasma of chimpanzee (CH413) having known infectious unit of $10^7$ CIU/ml (chimpanzee infectious units/ml) (FIG. 8, Lane 2). Human plasma (T.S) known to have $10^6$ CIU/ml also showed the similar length of band but its amount was about 1/10 of that of the aforementioned chimpanzee having $10^7$ CIU/ml. Patterns on the extreme left of the figure are those of molecular markers.

(10) Seroconversion of GORa Antibody in Acute NANB Hepatitis Patient

Table 4 contains data from a nurse who had been accidentally exposed to a needle stick contaminated with blood from a non-A, non-B hepatitis patient resulting in an acute hepatitis. As the table shows, there was no GORa antibody before infection and it was detected only after infection. At the initial stage of infection, GORa antibody of the IgM class was also positive. Emergence of HCV antibody, on the other hand, was very late. At the 8th week after infection, GORa antibody was already positive, while Chiron's HCV antibody was negative (Ortho HCV Ab ELISA test; Ortho Diagnostic Systems, Tokyo, Japan) until the 17th week after infection; this proves that, at least for this case, serological diagnosis of NANB hepatitis infection at an early stage is possible only with GORa antibody. Expression of IgM class GORa antibody in the acute phase presents another important significance. It is not easy to discern between an acute exacerbation of chronic hepatitis and acute hepatitis. They can, however, be distinguished by testing for GORa antibody IgM class and accurate diagnosis becomes possible.

The antigens and antibodies of the invention provide diagnostic reagents capable of quicker and wider range of diagnosis of NANB hepatitis than any other conventional reagent, and can be used at blood centers, blood derivatives manufacturers, transfusion departments of hospitals and many other places for elimination of blood carrying the NANB hepatitis agent from transfusion blood and blood derivatives. Screening tests by the diagnostic reagents using the antigen and antibodies under this invention will provide optimum means for prevention of post transfusion hepatitis which has long been a grave concern.

The nucleic acids and protein under this invention are manufactured not only as important reagents for serological and virological study of NANB hepatitis causative agent and for pathological study of the disease caused by it, but also as indispensable materials for manufacture of the aforementioned antigens and antibodies.

U.S. patent application Ser. No. 07/540,604, filed on Jun. 19, 1990, is hereby incorporated by reference for its teachings that the materials of the present invention may be utilized in detection kits and as vaccines.

Further variations and modifications of the invention will become apparent to those skilled in the art from the foregoing and are intended to be encompassed by the claims appended hereto.

Japanese Priority Applications 028191/90 filed Feb. 9, 1990; 153887/90 filed Jun. 14, 1990; 335806/90 filed Nov. 30, 1990; and 104010/91 filed Feb. 8, 1991 are relied on and incorporated by reference in their entirety.

TABLE 1

GORa antibody detected in patients with chronic liver disease

| No. | Patient | Diagnosis | GORa Antibody | * HCV Antibody |
|---|---|---|---|---|
| 1 | A.O. (M) | Chronic hepatitis/B | − | − |
| 2 | M.O. (M) | " | − | − |
| 3 | S.F. (M) | " | − | − |
| 4 | Y.I. (M) | " | + | + |
| 5 | H.N. (M) | " | − | − |
| 6 | T.O. (M) | " | − | − |
| 7 | S.Y. (F) | " | − | − |
| 8 | K.G. (M) | " | − | − |
| 9 | A.I. (M) | " | − | − |
| 10 | K.N. (M) | " | − | − |
| 11 | H.K. (M) | " | − | − |
| 12 | N.T. (M) | " | − | − |
| 13 | Y.T. (M) | " | − | − |
| 14 | T.K. (M) | " | − | − |
| 15 | K.A. (M) | " | − | − |
| 16 | K.S. (M) | " | + | + |
| 17 | T.N. (F) | " | − | − |
| 18 | H.T. (M) | " | − | − |
| 19 | K.G. (F) | " | − | − |
| 20 | T.T. (M) | " | − | − |
| 21 | T.S. (M) | " | − | − |
| 22 | U.A. (M) | " | − | − |
| 23 | S.T. (M) | " | − | − |
| 24 | S.O. (M) | " | − | − |
| 25 | M.W. (M) | " | − | − |
| 26 | T.S. (M) | " | − | − |
| 27 | T.S. (M) | " | + | − |
| 28 | F.N. (M) | Chronic hepatitis/Non-B | + | + |
| 29 | G.O. (M) | " | + | + |
| 30 | M.O. (M) | " | + | + |
| 31 | R.F. (M) | " | + | + |
| 32 | S.K. (F) | " | + | − |
| 33 | Y.M. (M) | " | + | + |
| 34 | T.Y. (F) | " | − | + |
| 35 | T.Y. (M) | " | + | + |
| 36 | Y.K. (M) | " | − | − |
| 37 | K.I. (M) | " | + | + |
| 38 | K.O. (F) | " | + | + |
| 39 | H.S. (M) | " | + | + |
| 40 | A.H. (F) | " | + | + |
| 41 | K.I. (M) | " | + | + |
| 42 | K.G. (M) | " | − | − |
| 43 | Y.K. (M) | " | + | + |
| 44 | M.S. (M) | " | + | + |
| 45 | C.A. (F) | " | + | − |
| 46 | M.Y. (F) | " | + | + |
| 47 | K.I. (F) | " | + | + |
| 48 | R.N. (M) | " | + | − |
| 49 | F.F. (F) | " | + | − |
| 50 | T.M. (M) | " | + | + |
| 51 | H.K. (F) | " | + | + |
| 52 | H.S. (F) | " | + | + |
| 53 | Y.K. (M) | " | − | + |
| 54 | T.I. (F) | " | + | + |
| 55 | S.? (F) | Chronic hepatitis/Non-B | + | + |
| 56 | H.M. (M) | " | + | − |
| 57 | S.A. (F) | " | + | − |
| 58 | Y.M. (M) | Liver Cirrhosis/B | − | + |
| 59 | N.Y. (M) | " | − | − |
| 60 | H.I. (M) | " | − | − |
| 61 | S.K. (M) | " | − | − |
| 62 | M.K. (M) | " | − | − |
| 63 | H.F. (F) | " | − | − |
| 64 | S.A. (M) | " | − | − |
| 65 | Y.F. (M) | " | − | − |
| 66 | T.F. (F) | " | − | − |
| 67 | K.K. (F) | " | − | − |
| 68 | T.K. (M) | " | + | + |
| 69 | M.N. (M) | Liver Cirrhosis/Non-B | − | + |
| 70 | K.O. (F) | " | + | + |
| 71 | K.M. (M) | " | + | + |
| 72 | F.K. (F) | " | + | + |
| 73 | H.S. (F) | " | + | + |
| 74 | H.O. (F) | " | + | + |
| 75 | T.I. (M) | " | − | + |
| 76 | Y.A. (F) | " | + | − |
| 77 | T.K. (M) | " | + | − |
| 78 | S.F. (M) | " | − | + |
| 79 | Y.I. (M) | " | + | + |
| 80 | H.H. (F) | " | + | − |
| 81 | R.S. (M) | " | + | + |
| 82 | ?.N. (M) | " | + | + |
| 83 | K.K. (M) | " | − | + |
| 84 | K.Y. (M) | Liver Cirrhosis/Non-B | + | − |
| 85 | K.T. (F) | " | + | + |
| 86 | G.N. (M) | " | + | + |
| 87 | T.S. (M) | Hepatoma/B | − | − |
| 88 | N.T. (M) | " | − | − |
| 89 | T.Y. (M) | Hepatoma/Non-B | − | − |
| 90 | M.I. (F) | " | + | + |
| 91 | R.A. (M) | " | − | + |
| 92 | J.S. (M) | " | − | − |
| 93 | K.S. (M) | " | + | − |
| 94 | S.K. (M) | " | + | − |
| 95 | T.T. (M) | " | − | − |

TABLE 1-continued

GORa antibody detected in patients with chronic liver disease

| No. | Patient | Diagnosis | GORa Antibody | * HCV Antibody |
|---|---|---|---|---|
| 96 | S.A. (M) | " | + | + |
| 97 | H.A. (M) | " | − | − |
| 98 | U.K. (F) | Hepatoma/B | + | + |
| 99 | ?.O.(M) | " | + | + |
| 100 | H.O. (M) | " | + | + |

Remarks:
1) "B" and "Non-B" in the "Diagnosis" column denote patients clearly associated with hepatitis B virus and those not associated with the virus respectively.
2) * column shows result of assays by Ortho HCV Ab ELISA test kit for comparison purpose.
3) (M) and (F) in "Patient" column designate male and female respectively.

TABLE 2

Frequency of NANB GORa antibody in patients with liver diseases

| Disease Group | Number of Patient | Frequency of GORa Antibody Number (Rate) | * HCV Antibody |
|---|---|---|---|
| Chronic hepatitis/B | 27 | 3 (11%) | 2 (7%) |
| Chronic hepatitis/Non-B | 30 | 27 (90%) | 21 (70%) |
| Liver cirrhosis/B | 11 | 1 (9%) | 3 (27%) |
| Liver cirrhosis/Non-B | 18 | 14 (78%) | 14 (78%) |
| Hepatoma/B | 2 | 0 (0%) | 0 (0%) |
| Hepatoma/Non-B | 12 | 7 (58%) | 6 (50%) |
| B Total | 40 | 4 (10%) | 5 (13%) |
| Non-B Total | 60 | 48 (80%) | 41 (68%) |
| Grand Total | 100 | 52 (52%) | 46 (46%) |

Remarks:
* column shows for comparison number (rate) of samples tested positive for HCV in Table 1.

TABLE 3

GORa antibody detected in donors with malfunctioning liver.

| Donor No. | GORa Antibody | * HCV Antibody | Donor No. | GORa Antibody | * HCV Antibody |
|---|---|---|---|---|---|
| 1 | − | − | 22 | − | − |
| 2 | − | − | 23 | + | + |
| 3 | − | − | 24 | + | − |
| 4 | − | − | 25 | − | + |
| 5 | − | − | 26 | − | − |
| 6 | − | − | 27 | − | − |
| 7 | − | − | 28 | − | − |
| 8 | − | − | 29 | − | − |
| 9 | − | − | 30 | + | + |
| 10 | − | − | 31 | − | − |
| 11 | − | − | 32 | + | + |
| 12 | − | − | 33 | − | − |
| 13 | − | − | 34 | − | − |
| 14 | − | − | 35 | − | − |
| 15 | − | + | 36 | + | − |
| 16 | − | − | 37 | − | − |
| 17 | − | − | 38 | + | + |
| 18 | − | − | 39 | − | − |
| 19 | − | − | 40 | − | − |
| 20 | − | − | 41 | N.T. | − |
| 21 | + | + | 42 | + | − |

Remarks:
1) For comparison purpose, * column shows the result of samples tested for Chiron's HCV antibody.
2) All samples were tested negative for hepatitis B virus antigen. As demonstrated in Table 2, 90% of Non-B chronic hepatitis samples were tested positive for GORa antibody, while only 20% of those "consciously healthy" population were positive for the antibody since such liver malfunction derives not only from the virus but from obesity and alcohol.
3) "N.T." means "not tested".

TABLE 4

Seroconversion of GORa in an acute non-A, non-B hepatitis patient

| Time (Week) | ALT | GORa Antibody IgM | GORa Antibody IgG | * (HCV Antibody) |
|---|---|---|---|---|
| 0 | 13 | − | − | − |
| 4 | 32 | N.T. | N.T. | − |
| 7 | 889 | N.T. | N.T. | − |
| 8 | 381 | + | + | − |
| 11 | 5 | + | ± | − |
| 14 | 20 | N.T. | N.T. | − |
| 17 | 41 | + | − | − |
| 19 | 15 | N.T. | N.T. | + |
| 21 | 77 | N.T. | N.T. | + |
| 22 | 38 | + | − | + |
| 27 | 18 | + | − | + |
| 250 | N.T. | ± | N.T. | N.T. |

*Remarks:
1) Above table shows a case of a nurse infected with hepatitis by needle prick accident. Time indicates number of week(s) elapsed after the accident. The patient, the source of the blood collected, was also tested positive for GORa antibody.
2) Result of the tests for Chiron's HCV are shown in * column for comparison.
3) N.T. means "not tested".

TABLE 5

Comparison of EIA using spGOR2 antibody and Western blot analysis using fusion protein

| No. | EIA | West. | No. | EIA | West. | No. | EIA | West. | No. | EIA | West. |
|---|---|---|---|---|---|---|---|---|---|---|---|
| 1 | 28 | − | 26 | >2000 | + | 51 | 1603 | + | 76 | 53 | − |
| 2 | 57 | − | 27 | 71 | − | 52 | 53 | − | 77 | >2000 | + |
| 3 | 107 | − | 28 | 63 | − | 53 | 55 | − | 78 | >2000 | + |

TABLE 5-continued

Comparison of EIA using spGOR2 antibody and Western blot analysis using fusion protein

| No. | EIA | West. | No. | EIA | West. | No. | EIA | West. | No. | EIA | West. |
|---|---|---|---|---|---|---|---|---|---|---|---|
| 4 | >2000 | + | 29 | 1557 | + | 54 | 1554 | + | 79 | >2000 | + |
| 5 | 474 | − | 30 | 37 | − | 55 | 52 | ± | 80 | >2000 | + |
| 6 | 50 | − | 31 | 34 | − | 56 | 1512 | + | 81 | 386 | ± |
| 7 | 134 | − | 32 | 87 | − | 57 | 910 | − | 82 | >2000 | + |
| 8 | >2000 | + | 33 | >2000 | + | 58 | >2000 | + | 83 | 1554 | + |
| 9 | 1662 | − | 34 | 102 | − | 59 | 35 | − | 84 | 896 | ± |
| 10 | 51 | − | 35 | 63 | − | 60 | 110 | ± | 85 | >2000 | + |
| 11 | 807 | ± | 36 | 61 | − | 61 | 29 | − | 86 | 49 | − |
| 12 | 62 | − | 37 | 32 | − | 62 | 1941 | + | 87 | 75 | − |
| 13 | 101 | − | 38 | 1039 | + | 63 | 55 | − | 88 | 1630 | + |
| 14 | 99 | − | 39 | 30 | − | 64 | 789 | + | 89 | 33 | − |
| 15 | 1886 | + | 40 | 1731 | + | 65 | >2000 | + | 90 | 1283 | + |
| 16 | >2000 | + | 41 | 49 | − | 66 | 1945 | + | 91 | >2000 | + |
| 17 | 77 | − | 42 | 265 | ± | 67 | 53 | − | 92 | 35 | − |
| 18 | >2000 | + | 43 | >2000 | + | 68 | 200 | − | 93 | 64 | − |
| 19 | 397 | ± | 44 | 51 | − | 69 | 39 | − | 94 | >2000 | + |
| 20 | 80 | − | 45 | 98 | − | 70 | 119 | − | 95 | 101 | ± |
| 21 | >2000 | − | 46 | 34 | − | 71 | 167 | − | 96 | >2000 | + |
| 22 | >2000 | + | 47 | >2000 | + | 72 | 1582 | + | 97 | 69 | ± |
| 23 | >2000 | + | 48 | >2000 | + | 73 | 469 | − | 98 | 729 | ± |
| 24 | >2000 | + | 49 | 87 | − | 74 | >2000 | + | 99 | >2000 | + |
| 25 | 68 | − | 50 | >2000 | + | 75 | 607 | + | 100 | 807 | ± |

Remarks: "West." indicates Western blot analysis

---

What is claimed:

1. A method for detecting non-A, non-B hepatitis related antigens in a sample comprising:
   (a) reacting said sample with non-A, non-B hepatitis related specific monoclonal or polyclonal antibodies directed to an antigen according to SEQ ID NOS:2 or 7–11 or an NANB hepatitis related epitope of a peptide, said NANB hepatitis related epitope comprising an amino acid chain of ten or more consecutive amino acids of SEQ ID NO:2, with said antibodies attached to a solid substrate under conditions which allow the formation of an antigen-antibody complex;
   (b) reacting the product of step (a) with non-A, non-B hepatitis related specific monoclonal or polyclonal antibodies directed to the antigen according to SEQ ID NOS:2 or 7–11 or an NANB hepatitis related epitope of a peptide, said NANB hepatitis related epitope comprising an amino acid chain of ten or more consecutive amino acids of SEQ ID NO:2 which antibodies are labelled; and
   (c) detecting the presence of labelled antibodies.

2. A non-A, non-B hepatitis related specific monoclonal or polyclonal antibody reactive with an antigen comprising the amino acid sequence according to SEQ ID NOS:2 or 7–12 or an NANB hepatitis related epitope of a peptide, said NANB hepatitis related epitope comprising an amino acid chain of ten or more consecutive amino acids of SEQ ID NO:2.

3. A non-A, non-B hepatitis diagnostic test kit for analyzing samples for the presence of a non-A, non-B hepatitis related antigen, comprising at least one non-A, non-B hepatitis related specific monoclonal or polyclonal antibody directed to the antigen according to SEQ ID NOS:2 or 7–11 or an NANB hepatitis related epitope of a peptide, said NANB hepatitis related epitope comprising an amino acid chain of ten or more consecutive amino acids of SEQ ID No:2, with said antibodies attached to a solid substrate and the non-A, non-B hepatitis related specific monoclonal or polyclonal antibodies directed to the antigen according to SEQ ID NOS:2 or 7–11 or an NANB hepatitis related epitope of a peptide, said NANB hepatitis related epitope comprising an amino acid chain of ten or more consecutive amino acids of SEQ ID NO:2 which antibodies are labelled.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2070 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GAATTCCCCC TGCCCTCTGA TCAGCCTGCC CAGAGCTTCG GGCTCCGGGT GCCCCAGATG      60
CACAACCAGG CCTCCGCATT TGTGGACATC CAGGCGGAGC CCCAGAACAG GGGTCCGGCG     120
GTGCCCCCAG CGTGTCTCAA GATGGTGACG GAGGCGTCCT ACTTCCCTGC GCAGAGGGA     180
TCGGCCTGCT GCTTGCCAGC CGCCCCAAGG CTGACAGAGA GGCCCTCGGG AGTCCGCATC     240
TCAGCCCCCA GGAAGAGGAA GACGATCGCC CAATCTTCCA GCCCTTGCTT GGTCACAGGT     300
TGCACAGATG CCAAGAGAAC CCGGGTGGCC AGCAGCAGCC AACGCTCCAG TGGCTCCAAG     360
GTCGGCAGAC AGCCAGGGAA GACGCGCAAC AGGTCAGGGA TGGCATGCAA GACCACCACC     420
ACCATCAGCT CTAAGCGAAT CGTCCGTCGT CCATCCCTAC CGAGTTTGAA GAAACCTATT     480
ATCCTAAGAA GGTCTGGGTG CCAAGTCCCC ACCGTCCTCC GCCGAGGCTA TCTCCAACTG     540
TTCACCGAAG AGTGTCTCAA GTTCTGCGCC TCCAAGCAGG AGGCCGTGGA GAAGGCGCTG     600
AACGAGGAGA AGGTGGCCTA CGACTGCAGC CCCAACAAGA ACAGGTACCT GAACGTGGTC     660
CTGAACACCC TCAAGAGACT GAAGGGCCTG ACCCCAGCT CCATGCCGGG CCTCAGCAGG      720
GCCGCCCTGT ACAGCCGCCT CCAGGAGTTC CTGCTCAGCC AGGACCAGCT CAAGGAGAAC     780
GGCTACCCCT TCCCGCACCC CGAGCGGCCC GGAGGCGCCG TCCTCTTCAC TGGCCAGGGG     840
AAGGGGCCCG GCGACTCCTC CTGCAGGGTC TGCTGCCGTT GTGGCACCGA GTACCTGGTG     900
```

```
TCCTCCTCGG GCCGCTGTGT ACGCGACCAG TTGTGTTATT ATCACTGGGG GCGGGTCCGC        960
TCGAGCCAGG TGGCTGGAGG CCGGGTTAGC CAGTACACCT GCTGTGCAGC TGCTCCTGGC       1020
TCTGTGGGCT GCCAGGTGGC AAAGCAGCAC GTGCGGGACG GCCGCAAGGA CAGCCTCGAT       1080
GGCTTCGTGG AGACCTTCAA GAAAGAGTTG TCCAGAGACG CTTATCCAGG AATCTACGCC       1140
TTGGACTGTG AGATGTGCTA CACCACGCAT GGCCTAGAGC TGACCCGCGT CACCGTGGTG       1200
GACGCCGACA TGCGAGTGGT GTACGACACC TTCGTCAAGC CGACAACGA  GATCGTGGAC       1260
TACAACACCA GGTTTTCCGG AGTCACCGAG GCCGACGTCG CCAAGACGAG CATCACCTTG       1320
CCCCAAGTGC AAGCCATCCT GCTGAGCTTT TTCAGCGCCC AAACCATCCT CATCGGGCAC       1380
AGCCTGGAGA GCGATCTGCT GGCCCTGAAG CTCATCCACA GCACCGTGCT GGACACGGCC       1440
GTGCTCTTCC CGCACTACCT GGGTTTCCCC TACAAGCGTT CCCTCAGGAA TCTCGCGGCC       1500
GACTACCTGG GACAGATCAT CCAGGACAGC CAGGACGGCC ACAAGTGGAG CGAGGACGCA       1560
AACGCCTGCC TGCAGCTGGT GATGTGGAAG GTCGACAGC  GCGCCCAGAT CCAGCCACGC       1620
CACCGGTCCG CCTCTCCCGC CGCCCTGGCC TGTCCTTGGC CCCAGGCCCC TTCCACAACC       1680
GCCATCAGTC CCGAGAGCTC ACCCTGTCCA CCTCGCCGCA AGGCCAAAGA AACCGGAGCA       1740
GTCGACGGCA GGAGAGGGCA AAAAGCCAAG AGTAACCCCA ACCGGCCACT CCCAGTCCCC       1800
CGGAATCCCT GCCGCGGACC CTCGGGCCTG TCCCCATCCC TCTGCCCTTC CCAGACCTCT       1860
GTCCTTCCAC TAATCGCCTC CCGCAGCACC GAGCCACCAC TCCCAGTCCC CCGAGTCCCT       1920
GCCGCGCCCC CTCGCGCCTG TCCACATCCC TCTGCCCATC CGAGACCTCT GTCCTTACAC       1980
CACTAGCCAC CCCACGTGGG ACTTCCATGG CCTCTGAGTA CAAGGCCAGC CCCCCGGCCC       2040
ACCAGCTTTC TGAATGTGTG CTTACCTGTT                                        2070
```

( 2 ) INFORMATION FOR SEQ ID NO:2:

( i ) SEQUENCE CHARACTERISTICS:
        ( A ) LENGTH: 661 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Glu Phe Pro Leu Pro Ser His Gln Pro Ala Gln Ser Phe Gly Leu Arg
 1               5                  10                  15

Val Pro Gln Met His Asn Gln Ala Ser Ala Phe Val Asp Ile Gln Ala
            20                  25                  30

Glu Pro Gln Asn Arg Gly Pro Ala Val Pro Pro Ala Cys Leu Lys Met
        35                  40                  45

Val Thr Glu Ala Ser Tyr Phe Pro Arg Gln Arg Gly Ser Ala Cys Cys
    50                  55                  60

Leu Pro Ala Ala Pro Arg Leu Thr Glu Arg Pro Ser Gly Val Arg Ile
65                  70                  75                  80

Ser Ala Pro Arg Lys Arg Lys Thr Ile Ala Gln Ser Ser Ser Pro Cys
                85                  90                  95

Leu Val Thr Gly Cys Thr Asp Ala Lys Arg Thr Arg Val Ala Ser Ser
            100                 105                 110

Ser Gln Arg Ser Ser Gly Ser Lys Val Gly Arg Gln Pro Gly Lys Thr
        115                 120                 125

Arg Asn Arg Ser Gly Met Ala Cys Lys Thr Thr Thr Ile Ser Ser
    130                 135                 140

Lys Arg Ile Val Arg Arg Pro Ser Leu Pro Ser Leu Lys Lys Pro Ile
```

-continued

```
145                      150                      155                          160
Ile Leu Arg Arg Ser Gly Cys Gln Val Pro Thr Val Leu Arg Arg Gly
                165                  170                  175
Tyr Leu Gln Leu Phe Thr Glu Glu Cys Leu Lys Phe Cys Ala Ser Lys
                180                  185                  190
Gln Glu Ala Val Glu Lys Ala Leu Asn Glu Lys Val Ala Tyr Asp
                195                  200                  205
Cys Ser Pro Asn Lys Asn Arg Tyr Leu Asn Val Val Leu Asn Thr Leu
        210                  215                  220
Lys Arg Leu Lys Gly Leu Thr Pro Ser Ser Met Pro Gly Leu Ser Arg
225                  230                  235                  240
Ala Ala Leu Tyr Ser Arg Leu Gln Glu Phe Leu Leu Ser Gln Asp Gln
                245                  250                  255
Leu Lys Glu Asn Gly Tyr Pro Phe Pro His Pro Glu Arg Pro Gly Gly
                260                  265                  270
Ala Val Leu Phe Thr Gly Gln Gly Lys Gly Pro Gly Asp Ser Ser Cys
                275                  280                  285
Arg Val Cys Cys Arg Cys Gly Thr Glu Tyr Leu Val Ser Ser Ser Gly
        290                  295                  300
Arg Cys Val Arg Asp Gln Leu Cys Tyr Tyr His Trp Gly Arg Val Arg
305                  310                  315                  320
Ser Ser Gln Val Ala Gly Gly Arg Val Ser Gln Tyr Thr Cys Cys Ala
                325                  330                  335
Ala Ala Pro Gly Ser Val Asp Cys Gln Val Ala Lys Gln His Val Arg
                340                  345                  350
Asp Gly Arg Lys Asp Ser Leu Asp Gly Phe Val Glu Thr Phe Lys Lys
                355                  360                  365
Glu Leu Ser Arg Asp Ala Tyr Pro Gly Ile Tyr Ala Leu Asp Cys Glu
        370                  375                  380
Met Cys Tyr Thr Thr His Gly Leu Glu Leu Thr Arg Val Thr Val Val
385                  390                  395                  400
Asp Ala Asp Met Arg Val Val Tyr Asp Thr Phe Val Lys Pro Asp Asn
                405                  410                  415
Glu Ile Val Asp Tyr Asn Thr Arg Phe Ser Gly Val Thr Glu Ala Asp
                420                  425                  430
Val Ala Lys Thr Ser Ile Thr Leu Pro Gln Val Gln Ala Ile Leu Leu
                435                  440                  445
Ser Phe Phe Ser Ala Gln Thr Ile Leu Ile Gly His Ser Leu Glu Ser
        450                  455                  460
Asp Leu Leu Ala Leu Lys Leu Ile His Ser Thr Val Leu Asp Thr Ala
465                  470                  475                  480
Val Leu Phe Pro His Tyr Leu Gly Phe Pro Tyr Lys Arg Ser Leu Arg
                485                  490                  495
Asn Leu Ala Ala Asp Tyr Leu Gly Gln Ile Ile Gln Asp Ser Gln Asp
                500                  505                  510
Gly His Asn Ser Ser Glu Asp Ala Asn Ala Cys Leu Gln Leu Val Met
        515                  520                  525
Trp Lys Val Arg Gln Arg Ala Gln Ile Gln Pro Arg His Arg Ser Ala
530                  535                  540
Ser Pro Ala Ala Leu Ala Cys Pro Trp Pro Gln Ala Pro Ser Thr Thr
545                  550                  555                  560
Ala Ile Ser Pro Glu Ser Ser Pro Cys Pro Pro Arg Arg Lys Ala Lys
                565                  570                  575
```

```
        Glu   Thr   Gly   Ala   Val   Asp   Gly   Arg   Arg   Gly   Gln   Lys   Ala   Lys   Ser   Asn
                          580                             585                             590

Pro   Asn   Arg   Pro   Leu   Pro   Val   Pro   Arg   Asn   Pro   Cys   Arg   Gly   Pro   Ser
                    595                             600                             605

Gly   Leu   Ser   Pro   Ser   Leu   Cys   Pro   Ser   Gln   Thr   Ser   Val   Leu   Pro   Leu
                    610                             615                             620

Ile   Ala   Ser   Arg   Ser   Thr   Glu   Pro   Pro   Leu   Pro   Val   Pro   Arg   Val   Pro
        625                             630                             635                             640

Ala   Ala   Pro   Pro   Arg   Ala   Cys   Pro   His   Pro   Ser   Ala   His   Pro   Arg   Pro
                                645                             650                             655

Leu   Ser   Leu   His   His
                          660
```

( 2 ) INFORMATION FOR SEQ ID NO:3:

( i ) SEQUENCE CHARACTERISTICS:
        ( A ) LENGTH: 166 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CCUGUCCACC   UCGCCGCAAG   GCCAAAGAAA   CCGGAGCAGU   CGACGGCAGG   AGAGGGCAAA        60

AAGCCAAGAG   UAACCCCAAC   CGGCCACUCC   CAGUCCCCCG   GAAUCCCUGC   CGCGGACCCU       120

CGGGCCUGUC   CCCAUCCCUC   UGCCCUUCCC   AGACCUCUGU   CCUUCC                        166
```

( 2 ) INFORMATION FOR SEQ ID NO:4:

( i ) SEQUENCE CHARACTERISTICS:
        ( A ) LENGTH: 166 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
GGAAGGACAG   AGGUCUGGGA   AGGGCAGAGG   GAUGGGGACA   GGCCCGAGGG   UCCGCGGCAG        60

GGAUUCCGGG   GGACUGGGAG   UGGCCGGUUG   GGGUUACUCU   UGGCUUUUUG   CCCUCUCCUG       120

CCGUCGACUG   CUCCGGUUUC   UUUGGCCUUG   CGGCGAGGUG   GACAGG                        166
```

( 2 ) INFORMATION FOR SEQ ID NO:5:

( i ) SEQUENCE CHARACTERISTICS:
        ( A ) LENGTH: 166 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
CCTGTCCACC   TCGCCGCAAG   GCCAAAGAAA   CCGGAGCAGT   CGACGGCAGG   AGAGGGCAAA        60

AAGCCAAGAG   TAACCCCAAC   CGGCCACTCC   CAGTCCCCCG   GAATCCCTGC   CGCGGACCCT       120

CGGGCCTGTC   CCCATCCCTC   TGCCCTTCCG   AGACCTCTGT   CCTTCC                        166
```

( 2 ) INFORMATION FOR SEQ ID NO:6:

( i ) SEQUENCE CHARACTERISTICS:
        ( A ) LENGTH: 166 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGAAGGACAG AGGTCTGGGA AGGGCAGAGG GATGGGGACA GGCCCGAGGG TCCGCGGCAG    60

GGATTCCGGG GGACTGGGAG TGGCCGGTTG GGGTTACTCT TGGCTTTTTG CCCTCTCCTG    120

CCGTCGACTG CTCCGGTTTG TTTGGCCTTG CGGCGAGGTG GACAGG    166

( 2 ) INFORMATION FOR SEQ ID NO:7:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Cys Pro Pro Arg Arg Lys Ala Lys Glu Thr Gly Ala Val Asp Gly Arg
 1               5                  10                 15

Arg Gly Gln Lys Ala Lys Ser Asn Pro Asn Arg Pro Leu Pro Val Pro
             20                  25                 30

Arg Asn Pro Cys Arg Gly Pro Ser Gly Leu Ser Pro Ser Leu Cys Pro
         35                  40                  45

Ser Gln Thr Ser Val Leu Pro
         50              55
```

( 2 ) INFORMATION FOR SEQ ID NO:8:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
Cys Pro Pro Arg Arg Lys Ala Lys Glu Thr Gly Ala Val Asp Gly Arg
 1               5                  10                 15

Arg Gly Gln Lys Ala Lys Ser Asn Pro Asn Arg Pro Leu
             20                  25
```

( 2 ) INFORMATION FOR SEQ ID NO:9:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Gly Arg Arg Gly Gln Lys Ala Lys Ser Asn Pro Asn Arg Pro Leu Pro
 1               5                  10                 15

Val Pro Arg Asn Pro Cys Arg Gly Pro Ser Gly
             20                  25
```

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

```
Gly Arg Arg Gly Gln Lys Ala Lys Ser Asn Pro Asn Arg Pro Leu
 1               5                  10                 15
```

( 2 ) INFORMATION FOR SEQ ID NO:11:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( x i ) SEQUENCE DESCRIPTION: SEQ ID NO:11:

Val Ala Lys Gln His Val Arg Asp Gly Arg Lys Asp Ser Leu Asp Gly
1               5                   10                  15

Phe Val ( 2 ) INFORMATION FOR SEQ ID NO:12:

( i ) SEQUENCE CHARACTERISTICS:
    ( A ) LENGTH: 26 amino acids
    ( B ) TYPE: amino acid
    ( C ) STRANDEDNESS: single
    ( D ) TOPOLOGY: linear ( x i ) SEQUENCE DESCRIPTION: SEQ ID NO:12:

Leu Pro Val Pro Arg Asn Pro Cys Arg Gly Pro Ser Gly Leu Ser Pro
1               5                   10                  15

Ser Leu Cys Pro Ser Gln Thr Ser Val Leu
            20                  25